(12) United States Patent
Hollemann et al.

(10) Patent No.: US 10,312,659 B1
(45) Date of Patent: Jun. 4, 2019

(54) CONTROLLING LASER BEAM PARAMETERS BY CRYSTAL SHIFTING

(71) Applicant: Coherent LaserSystems GmbH & Co. KG, Göttingen (DE)

(72) Inventors: Guenter Hollemann, Luebeck (DE); Axel Kneip, Kiel (DE)

(73) Assignee: COHERENT LASERSYSTEMS GMBH & CO. KG, Göttingen (DE)

( * ) Notice: Subject to any disclaimer, the term of this patent is extended or adjusted under 35 U.S.C. 154(b) by 0 days.

(21) Appl. No.: 15/926,178

(22) Filed: Mar. 20, 2018

(51) Int. Cl.
*G02F 1/35* (2006.01)
*H01S 3/13* (2006.01)
*G01J 1/42* (2006.01)

(52) U.S. Cl.
CPC .............. *H01S 3/13* (2013.01); *G01J 1/4257* (2013.01); *G02F 1/353* (2013.01); *G02F 1/3525* (2013.01); *G01J 2001/4261* (2013.01)

(58) Field of Classification Search
CPC ......... G02F 1/3525; H01S 3/13; H01S 3/1305
See application file for complete search history.

(56) References Cited

U.S. PATENT DOCUMENTS

| | | | |
|---|---|---|---|
| 5,064,284 A | 11/1991 | Johnston, Jr. et al. | |
| 5,214,485 A | 5/1993 | Sasnett et al. | |
| 5,825,562 A | 10/1998 | Lai et al. | |
| 6,765,201 B2* | 7/2004 | Uto | G01N 21/956 850/8 |
| 6,816,316 B2* | 11/2004 | Caudle | G02B 26/06 359/618 |
| 6,859,335 B1 | 2/2005 | Lai et al. | |
| 6,890,474 B2 | 5/2005 | Gruber et al. | |
| 6,914,733 B2* | 7/2005 | Dong | G02B 7/008 359/819 |
| 7,366,214 B2* | 4/2008 | Liu | H01S 3/13 372/38.02 |
| 8,482,846 B2 | 7/2013 | Kneip | |
| 8,976,343 B2 | 3/2015 | Genis | |
| 9,429,814 B2* | 8/2016 | Zanger | G02F 1/3525 |
| 9,823,435 B2* | 11/2017 | Ziolek | G02B 7/005 |

* cited by examiner

*Primary Examiner* — Rhonda S Peace
(74) *Attorney, Agent, or Firm* — Morrison & Foerster LLP

(57) ABSTRACT

This disclosure provides methods and apparatuses which advantageously stabilize beam parameters and elongate crystal lifetime. In one aspect, a UV laser apparatus includes a non-linear crystal, a laser source, a beam-crystal displacer, a beam parameter monitor, and a laser control unit. The laser source directs a source beam to the non-linear crystal to produce a UV beam and the beam-crystal displacer shifts the non-linear crystal relative to the source beam at a plurality of shift speeds. The beam parameter monitor measures the UV beam and outputs a measurement of a beam parameter. The laser control unit: receives the measurement; determines, based on the measurement, an adjustment in shift speed that steers the beam parameter toward a target value; and outputs the adjustment to the beam-crystal displacer.

34 Claims, 6 Drawing Sheets

CONTROLLING LASER BEAM PARAMETERS BY CRYSTAL SHIFTING

TECHNICAL FIELD

This disclosure relates in general to stabilizing ultraviolet (UV) beam parameters. This disclosure relates in particular to varying a shift speed of a non-linear crystal to control a UV beam parameter.

BACKGROUND

Typically, laser apparatuses generate UV beams by directing a source beam to a non-linear crystal. Within the crystal, the source beam is frequency converted to a higher frequency, producing a shorter wavelength beam. For example, a 532 nm beam can be directed to a non-linear crystal to generate a 266 nm beam (the second harmonic wavelength of the 532 nm beam). For example, a 1064 nm beam and a 532 nm beam can generate a 355 nm beam (the third harmonic wavelength of the 1064 nm beam). Sometimes multiple crystals are necessary to convert a source beam to a desired UV beam wavelength.

Many processes require very stable UV beam parameters. Semiconductor wafer inspection processes, for example, tolerate less than 5 percent beam parameter drift over time. With UV processing, the beam parameter can drift as the non-linear crystal degrades. UV beam parameter drift manifests as unstable beam quality ($M^2$), unstable axial beam waist location ($z_0$), and unstable beam waist diameter ($2\omega_0$) (among others).

When source beams are frequency converted using a non-linear crystal, UV beam parameters can degrade due to bulk or surface degradation of the crystal. Bulk degradation can result from photo-assisted modifications of the crystal along the beam path inside the crystal and from related "compaction" of optical material. Bulk degradation causes increased thermal dephasing, and wavefront distortion, related to increasing absorption of the source and UV beams. Surface degradation can result from photo-assisted deposition and decomposition of contaminants of the crystal environment or by gradual destruction of the crystal surface (leading to unwanted wave front distortions or diffraction effects).

Existing solutions to address UV beam degradation include shifting the source beam to a new spot on the crystal when beam parameters hit specification limits (see, e.g., U.S. Pat. No. 8,976,343). This approach extends crystal life, but disadvantageously leads to step-wise changes in beam parameters after spot shifting, which can impact laser tool performance. This approach does not address unstable beam parameters.

Existing solutions also include continuous shifting of the non-linear crystal relative to the incident beam (see, e.g., U.S. Pat. No. 8,482,846). This approach can further prolong crystal lifetime but does nothing to address unstable beam parameters.

Although existing solutions prolong crystal lifetime by reducing degradation rates of the crystal, those solutions do nothing to stabilize beam parameters.

SUMMARY

This disclosure provides methods and apparatuses which advantageously prolong the crystal lifetime and stabilize beam parameters. In one aspect, a UV laser apparatus includes a non-linear crystal, a laser source, a beam-crystal displacer, a beam parameter monitor, and a laser control unit. The laser source directs a source beam to the non-linear crystal to produce a UV beam and the beam-crystal displacer shifts the non-linear crystal relative to the source beam at a plurality of shift speeds. The beam parameter monitor measures the UV beam and outputs a measurement of a beam parameter. The laser control unit: receives the measurement; determines, based on the measurement, an adjustment in shift speed that steers the beam parameter toward a target value; and outputs the adjustment to the beam-crystal displacer.

In another aspect, a method for controlling a UV beam includes directing a source beam to a non-linear crystal to produce a UV beam; shifting the non-linear crystal relative to the source beam at a first shift speed; measuring a beam parameter of the UV beam; determining, based on the measured beam parameter, a second shift speed that steers the beam parameter toward a target value; and shifting the non-linear crystal relative to the source beam at the second shift speed.

BRIEF DESCRIPTION OF THE DRAWINGS

The accompanying drawings, which are incorporated in and constitute a part of the specification, schematically illustrate preferred embodiments, and together with the general description given above and the detailed description of the embodiments given below, serve to explain principles of the inventions.

DETAILED DESCRIPTION

Methods and apparatuses described herein vary a lateral shift speed of a non-linear crystal to steer a UV beam parameter toward a target value. Embodiments described herein are especially suitable for crystals that degrade during UV exposure and then show partial or total recovery without UV exposure. Some embodiments avoid large drift of beam parameters or power loss even at very high UV power. Further advantages may include a smaller initial beam parameter drift after start or restart of the laser, reduced or eliminated beam parameter changes after spot shifts, and very slow long term degradation of the crystal (resulting in much longer crystal life).

Figure 1:
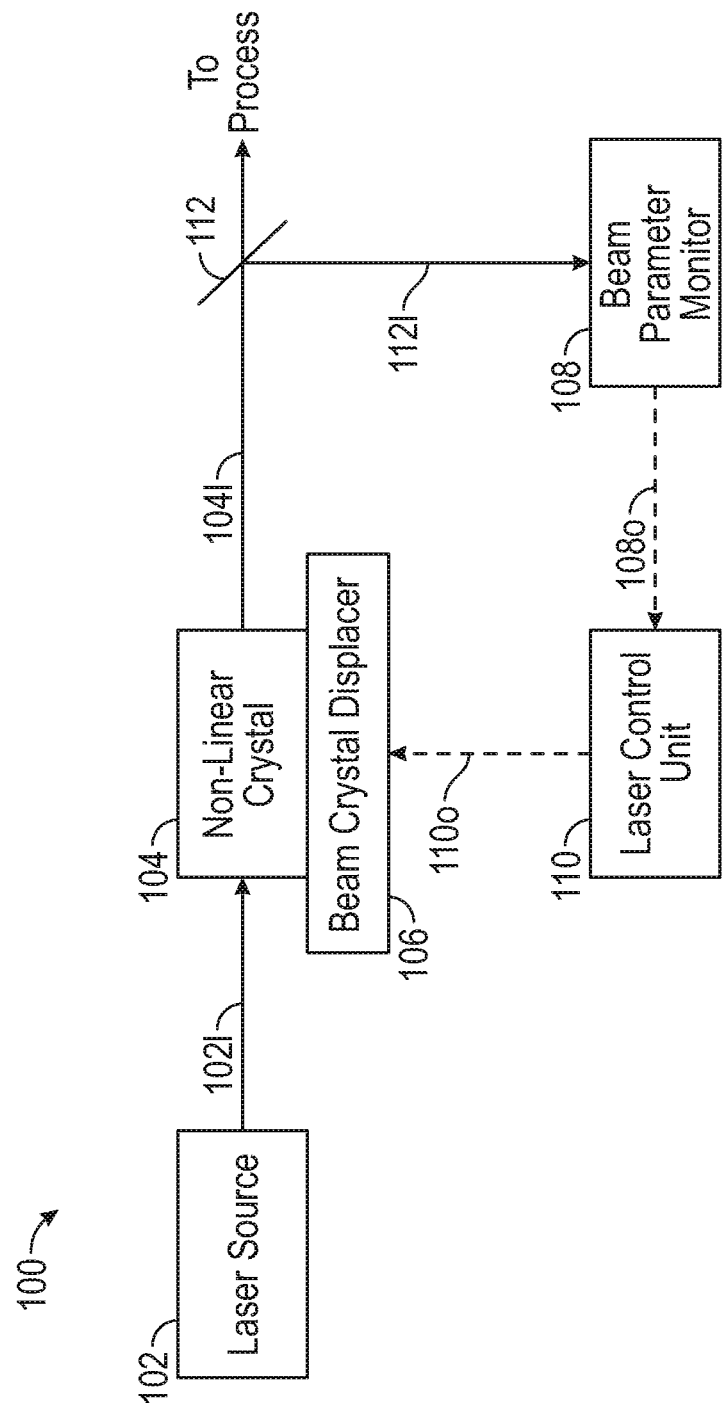
FIG. 1 depicts an embodiment of a UV laser apparatus.

Turning now to the drawings, where like features are designated by like reference numerals, FIG. 1 depicts an embodiment of a UV laser apparatus 100. Laser apparatus 100 includes a laser source 102, a non-linear crystal 104, a beam-crystal displacer 106, a beam parameter monitor 108, and a laser control unit 110. Apparatus 100 may vary the shift speed of non-linear crystal 104 to steer a UV beam parameter toward a target value.

Laser source 102 directs source beam 102*l* to non-linear crystal 104 to produce UV beam 104*l*. Source beam 102*l* can be continuous or pulsed. Typically, source beam 104*l* is focused in the non-linear crystal 104. In some embodiments, source beam 102*l* includes a spherical or an elliptical cross-section. A typical spherical beam diameter is 250 µm and a typical elliptical beam is 200 µm×500 µm. In some embodiments, the focused beam diameter is between 20 µm and 2 mm; smaller beam waists may be used for focusing in short crystals and larger beam waists may be used for ultrashort pulsed source laser beams.

In some embodiments, non-linear crystal 104 degrades during an exposure to the source beam and at least partially recovers after the exposure to the source beam. Where a non-linear crystal degrades during an exposure to the source beam and at least partially recovers after the exposure to the source beam, there will be a recovery time characteristic that will differ from material to material. Without being limited by a theory, the recovery may be an Arrhenius process that is thermally driven and has a characteristic recovery time. Non-linear crystal 104 can be any material sufficient to convert the frequency of source beam 102*l*. Examples for non-linear crystal 104 include (but are not limited to) borates, such as cesium lithium borate (CLBO), lithium triborate (LBO), and beta barium borate (BBO). Exemplary wavelengths for UV beam 104*l* include 355 nm, 266 nm, 244 nm, 213 nm, and less than 200 nm. Other wavelengths are contemplated.

Beam-crystal displacer 106 shifts non-linear crystal 104 relative to source beam 102*l*. In some embodiments, beam-crystal displacer 106 is a crystal-shifter having one or more translation stages. In some embodiments, a beam-crystal displacer translates the beam in space while the crystal is stationary.

Beam-crystal displacer 106 is able to shift the non-linear crystal 104 in at least one direction and at different speeds. In some embodiments, beam-crystal displacer 106 shifts a crystal in two directions at different speeds. In some embodiments, beam-crystal displacer 106 shifts non-linear crystal continuously. As used herein, continuous shifting includes approximately continuous shifting. For example, beam-crystal displacer 106 may be powered such that the crystal is moved in increments with a pause between movements. In some embodiments, beam-crystal displacer 106 shifts the crystal step-wise. For example, the crystal is moved to a spot, the crystal pauses at that spot for irradiation, and then moves to the next spot. In some embodiments, the beam spot on non-linear crystal 104 may overlap by 0-95% from spot to spot.

In some embodiments, the source beam 102*l* irradiates a spot for 10 seconds to 60 minutes and leaves 200 seconds to 1000 hours between irradiations of that spot. In some embodiments, the shift speed is non-zero and preferably varies from 0.00003 µm/s to 1 mm/s and more preferably from 0.001 µm/s to 1 µm/s. In some embodiments, the cycle time (time between consecutive radiations of the same spot) is preferably 1 min to 1,000 hours and more preferably 30 mins to 1,000 hours. In some embodiments, a source beam traces a closed path of preferably 0.5 to 500 mm in length and more preferably 0.5 to 50 mm in length. One of skill in the art will understand that these values are exemplary and other embodiments may use higher or lower values.

Beam parameter monitor 108 measures UV beam 104*l* and outputs (depicted in FIG. 1 by output connection 108*0*) a measurement of the beam parameter to laser control unit 110. In some embodiments, the beam parameter is a size or propagation parameter, such as one of beam quality, axial beam waist location, beam divergence, and beam waist diameter. As used herein, a "size or propagation parameter" does not include beam power or beam intensity.

Laser apparatus 100 optionally includes a beam splitter 112 to divert a portion (laser beam 112*l*) of the UV beam 104*l* to beam parameter monitor 108. In some embodiments, beam parameter monitor 108 includes a beam aperture in auxiliary beam 112*l* and a photodiode or some imaging system. In some embodiments, beam parameter monitor 108 includes a lens, an aperture, an optional diffuser, and a photo diode. The lens focuses the beam to form a beam caustic. The aperture is located at an appropriate location along the beam caustic; for example, at the beam waist location. The aperture allows transmission of a selected portion of the beam cross section. The optional diffuser is located in the transmitted beam. The photo diode is exposed to the transmitted beam that is optionally diffused. This arrangement can measure changes in the beam caustic, which correlate to a beam parameter change, by evaluating the photo diode signal. This embodiment can be implemented in laser apparatus 100 or in a process tool. In some embodiments, a one- or two-dimensional CCD device with corresponding evaluation electronics/software can be applied in lieu of the photo diode. In some embodiments, a portion of the beam is picked off to measure beam parameters (for example, with a commercial beam analyzer).

In some embodiments, beam parameter monitor 108 monitors a process property resulting from the UV beam's interaction with a process object. The process property might be a parameter of an object that responds to beam interaction. This arrangement could be utilized as part of a semi inspection tool. These tools typically record stray light, generated by a laser beam focus scanning a patterned or unpatterned wafer or mask. Optics, electronics, and software collect and evaluate the stray light to derive a number of parameters from the complex stray light data. These parameters include data that characterizes the focusing conditions and can be used to derive a figure of merit which contains information about $M^2$, lateral focus position, or beam focus diameter, as some examples. This figure of merit can be compared to a target value and fed to the laser control unit 110 which then determines if and how much the scanning speed needs to be accelerated or decelerated in a closed servo loop.

In some embodiments, beam parameter monitor 108 continuously measures UV beam 104*l*. It should be appreciated that continuous measurement includes approximately continuous measurement. Herein, "continuous measurement" means measurement at the maximum duty cycle of the beam parameter monitor.

In some embodiments, beam-crystal displacer 106 shifts non-linear crystal 104 so that the source beam 102 repeatedly traverses a path on the crystal and beam parameter monitor 108 measures the UV beam once during each completion of the path. In some embodiments, beam-crystal displacer 106 shifts non-linear crystal 104 so that the source beam 102 repeatedly traverses a path on the crystal and beam crystal displacer adjusts the shift speed at least once while traversing the complete path.

In some embodiments, the beam-crystal displacer shifts the non-linear crystal so that the source beam repeatedly traverses a path and the beam parameter monitor measures the UV beam at a refurbishment interval. Some embodiments include use of a commercial beam analyzer, for example a NanoModeScan from MKS Instruments Inc. of Andover Mass., a BeamSquared from MKS Instruments Inc., of Andover Mass., or a ModeMaster from Coherent Inc.

of Santa Clara Calif. Exemplary beam parameter monitors are disclosed in U.S. Pat. Nos. 5,064,284 and 5,214,485, the contents of which are incorporated herein in their entireties for all purposes. Measurement can be performed, for example, at monthly intervals to correct the shifting speed in order to recover the beam parameters to the set point.

Laser control unit 110 receives the beam parameter measurement, uses the measurement to determine an adjustment in shift speed that steers the beam parameter toward a target value, and then outputs (depicted by output connection 110*o*) the adjustment to the beam-crystal displacer 106. In some embodiments, the laser control unit 110 compares the beam parameter to a target value and calculates the shifting speed of beam-crystal displacer 106 to steer the beam parameter toward the target value. For example, when laser control unit 110 determines the beam parameter is above the value, laser control unit 110 outputs an increase in shift speed to beam-crystal displacer 106; when laser control unit 100 determines the beam parameter is below the value, laser control unit 110 outputs a decrease in shift speed to beam-crystal displacer 106. In other embodiments, when laser control unit 110 determines the beam parameter is above the value, laser control unit 110 outputs a decrease in shift speed to beam-crystal displacer 106; when laser control unit 100 determines the beam parameter is below the value, laser control unit 110 outputs an increase in shift speed to beam-crystal displacer 106.

In some embodiments, laser control unit 110 maintains the beam parameter within a target range. To that end, laser control unit 100 may accelerate and retard the shift speed to keep the beam parameter within the target range. For example, if the beam parameter measurement is above the target range (in other words, above an upper threshold of the target range), then laser control unit 110 sends a signal to increase the shifting speed (the signal provides, e.g., an incremental increase in shift speed or a set-speed above the current shifting speed); if the beam parameter measurement is below the target range (in other words, below a lower threshold of the target range), then laser control unit 110 sends a signal to decrease the shifting speed (the signal provides, e.g., an incremental decrease in shift speed or a set-speed below the current shifting speed).

In some embodiments, laser control unit 110 outputs the adjustment in shift speed as a command signal to the beam-crystal displacer 106. In some embodiments, beam parameter monitor 108, laser control unit 110, and beam-crystal displacer 106 act together as a servomechanism to achieve the target range.

In some embodiments, the laser control unit sets an initial shifting speed that is slow compared to an expected speed to achieve the target beam parameter. An initial shifting speed can be understood to be a speed of the beam-crystal displacer immediately after the laser is first turned on or a speed of the beam-crystal displacer when the laser is turned on after a prolonged period of off time. The prolonged period may be comparable to or longer than the recovery time of the crystal. In some embodiments, once the beam parameter has settled (after an initial period of beam parameter drift), laser control unit 110 may operate as described above: receive the beam parameter measurement, use the measurement to determine an adjustment in shift speed that steers the beam parameter toward a target value, and then output the determined adjustment in shift speed to the beam-crystal displacer 106. The frequency of measurement may be set before-hand, as described elsewhere herein. In some embodiments, the frequency of beam measurement may be dynamic: if the beam parameter measurements show little variation over time, the system may extend the intervals between measurements; if the beam parameter measurements show non-trivial variations in measurements (such as a rapid drop of beam parameter in a given interval), the system may shorten the intervals between measurements. This may advantageously reduce expenditure of system resources (e.g., frequency of beam parameter measurement) for crystals that show little degradation, while focusing such resources on crystals that do show degradation.

In some embodiments, laser control unit 110 continuously outputs an adjustment to the beam-crystal displacer 106. In some such embodiments, the continuously output adjustments result from beam parameter monitor 108 continuously measuring UV beam 104*l*.

Figure 2:
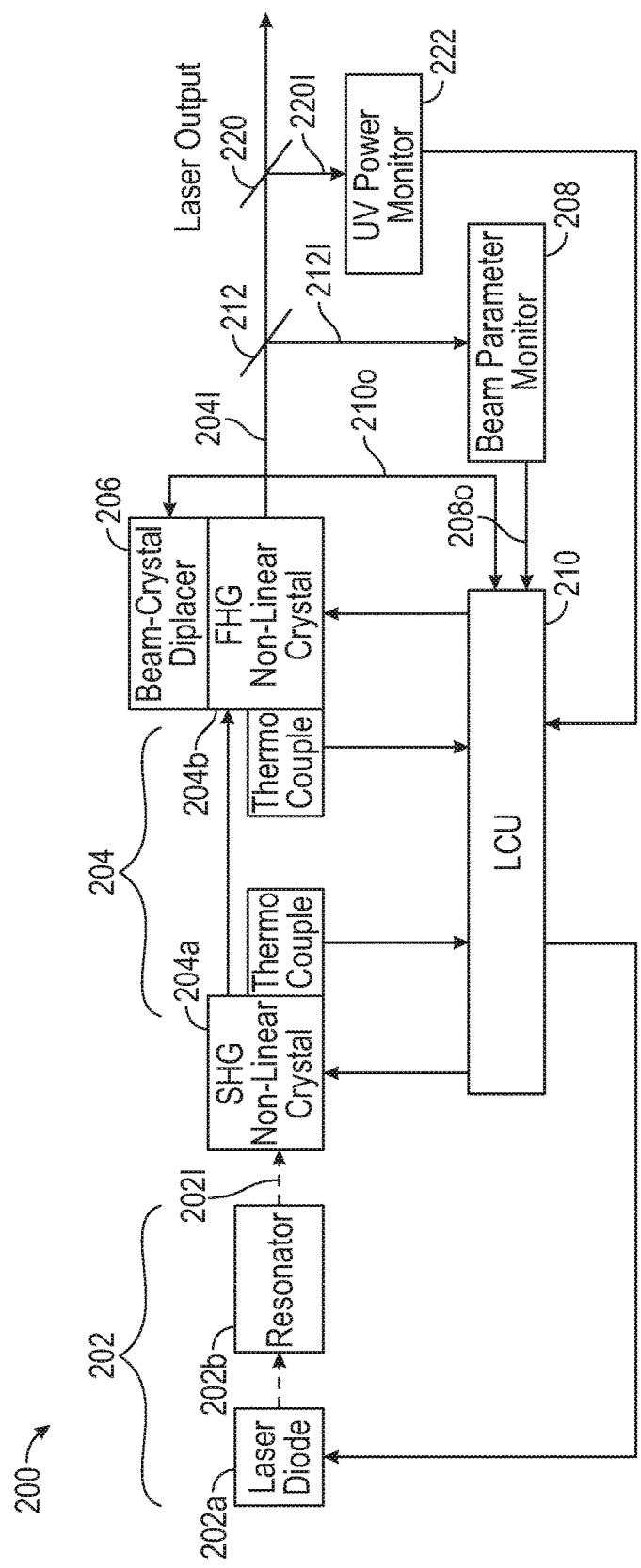
FIG. 2 depicts an embodiment of a UV laser apparatus.

FIG. 2 depicts an embodiment of a UV laser apparatus 200. Laser apparatus 200 includes a laser source 202, non-linear crystals 204*a* and 204*b*, a beam parameter monitor 208, a laser control unit 210, beam splitters 212 and 220, and power monitor 222. Like features in apparatus 200 are designated by like reference numerals as apparatus 100 and, for the sake of brevity, are not redescribed here with respect to FIG. 2.

Laser source 202 includes a laser diode 202*a* and a laser resonator 202*b*. Laser diode 202*a* optically energizes a gain medium in laser resonator 202*b*. Laser source 202 directs source beam 202*l* to non-linear crystals 204.

Laser apparatus 200 includes multiple non-linear crystals. The first non-linear crystal 204*a* is a second harmonic generator (SHG); non-linear crystal 204*a* takes a 1064 nm source beam and converts to a 532 nm beam. The second non-linear crystal 204*b* is a fourth harmonic generator (FHG); non-linear crystal 204*b* takes a 532 nm beam and outputs a 266 nm UV laser beam (204*l*).

FIG. 2 depicts beam crystal displacer 206 moving non-linear crystal 204*b*. In some embodiments, beam crystal displacer 206 is a translation stage. In some embodiments, a beam-crystal displacer shifts multiple non-linear crystals, for example both crystals 204*a* and 204*b*. In some embodiments, individual beam-crystal displacers shift each non-linear crystal so that the crystals are shifted independently. This may be advantageous for crystals that degrade at different rates or have different occlusion spots (i.e., spots to be avoided by the source beam).

Laser apparatus 200 includes beam parameter monitor 208. Beam splitter 212 diverts a portion 212*l* of UV beam 204*l* to the beam parameter monitor 208. The beam parameter monitor 208 takes a measurement of a beam parameter (e.g., beam quality) and outputs (via output 208*o*) the measurement to the laser control unit 210.

Laser control unit 210 receives (via output 208*o*) the beam parameter measurement from the beam parameter monitor 208, uses the measurement to determine an adjustment in shift speed that steers the beam parameter toward a target value, and then outputs (depicted by output connection 210*o*) the determined adjustment in shift speed to the beam crystal displacer 206. The laser control unit 210 also controls the oven temperatures for crystals 204*a* and 204*b* to maximize nonlinear conversion efficiency. Laser control unit 210 receives a temperature(s) from a thermocouple(s) and adjusts the temperature(s) of the oven(s) accordingly.

Laser apparatus 200 is also depicted in a light loop mode by use of UV power monitor 222 and laser control unit 210. A beam splitter 220 diverts a portion 220*l* to power monitor 222 which makes a measurement of the beam power. This measurement is then output to laser control unit 210, which regulates the laser diode 202a current thereby controlling the optical power directed into resonator 202b for energizing the gain medium.

Figure 3A:
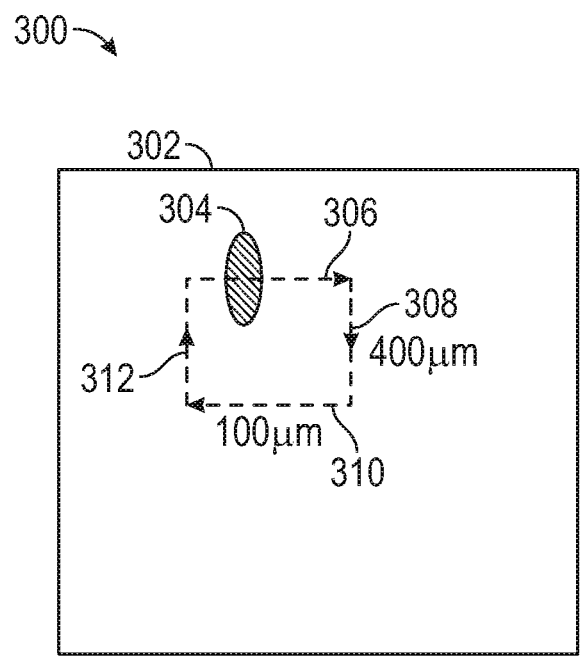
FIG. 3A depicts a path traversed by a laser beam on a non-linear crystal, in accordance with an embodiment.

FIG. 3A depicts an exemplary path 300 traversed by a laser beam on non-linear crystal 302. Beam spot 304 traverses a rectangular path, including a first horizontal section 306, a first vertical section 308, a second horizontal section 310, and second vertical section 312. In embodiment 300, the vertical sections are 400 µm and the horizontal sections are 100 µm. Note: the beam spot is not drawn to scale.

In some embodiments, a non-linear crystal exhibits both permanent and temporary degradation. In such crystals, when a laser beam traverses a complete path and restarts on that same path, some of the crystal has permanently degraded and the remainder has recovered. In some embodiments, a shifting speed may be adjusted as a path is completed to account for the permanent degradation of the crystal. In further embodiments, the shifting speed is adjusted after the path is first completed to account for permanent degradation of the crystal.

In some embodiments, the beam-crystal displacer shifts a non-linear crystal so that the source beam repeatedly traverses a path (for example, the path depicted in FIG. 3A) and a time between irradiations of a spot on the path is at least 20 times longer than an irradiation time of the spot.

In some embodiments, the beam-crystal displacer shifts the non-linear crystal so that the source beam traverses a limited, smaller area on the crystal. Here, a "limited smaller area" means an area that is relatively small compared to the overall cross-sectional area of the non-linear crystal. Preferably, an area that is less than 20% of the overall cross-sectional area, more preferably, less than 10% of the overall cross-sectional area. This may advantageously reduce large beam parameter fluctuations.

Figure 3B:
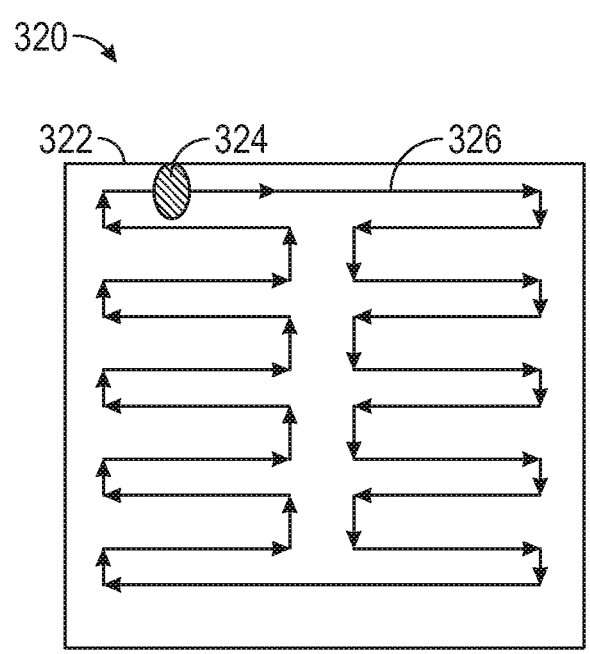
FIG. 3B depicts a path traversed by a laser beam on a non-linear crystal, in accordance with an embodiment.

FIG. 3B depicts an exemplary path 320 traversed by a laser beam on non-linear crystal 322. Path 320 includes linear sections 326, but instead of the rectangular path in embodiment 300, laser beam spot 324 traverses a path 320 that covers more of the non-linear crystal 322. When the beam spot 324 covers more of the non-linear crystal, the laser can advantageously operate at higher output power and faster shifting speed with the same stable beam parameters. In some embodiments, the shifting speed can be around 10 µm/min. Further, the longer length of path 320 may be helpful to avoid scanning of the total closed path in a short period of time, in order to allow a recovery time following exposure to the UV beam.

Figure 3C:
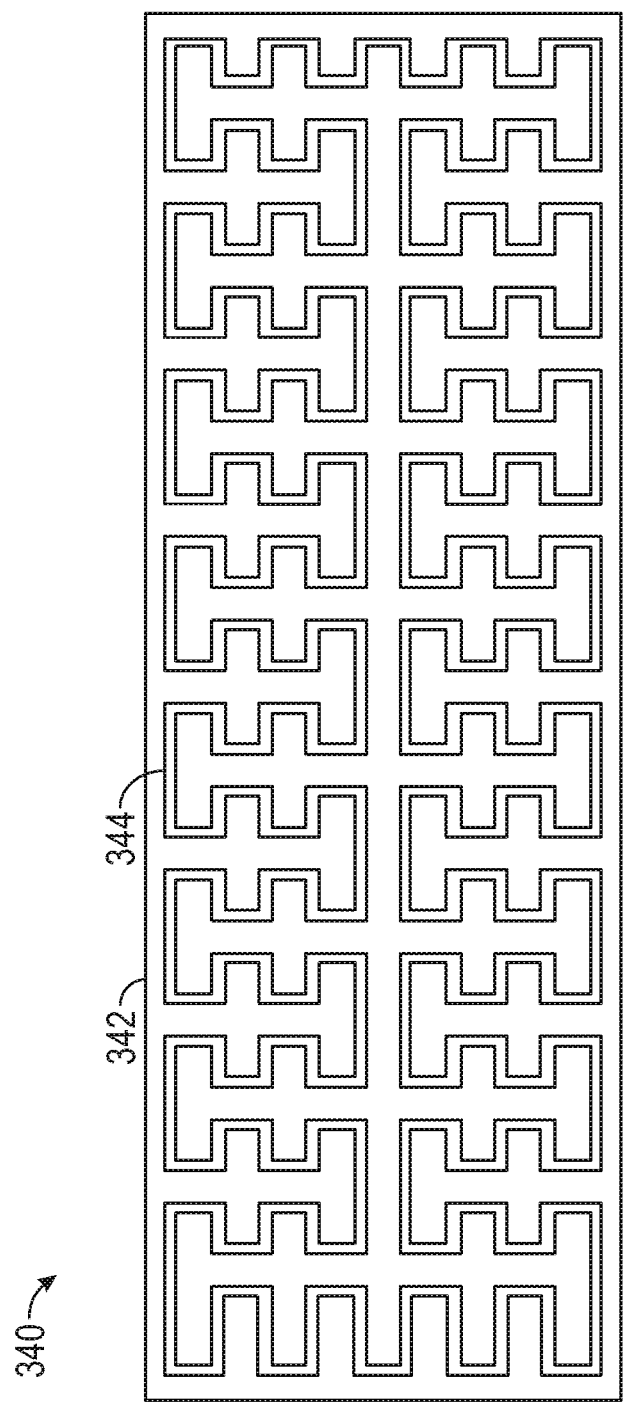
FIG. 3C depicts a path traversed by a laser beam on a non-linear crystal, in accordance with an embodiment.

FIG. 3C depicts an exemplary path 340 traversed by a laser beam (not shown) on non-linear crystal 342. Path 340 includes linear sections 346, but traverses a serpentine path. Path 340 covers more of the non-linear crystal 342 than path 320. In some embodiments, a beam-crystal displacer shifts the non-linear crystal so that the source beam traverses the serpentine path. Path 344 may be useful as it avoids large straight portions of path which can cause larger beam parameter drifts. For example, given a path of 1 mm and shifting speed of 0.1 µm/s, a laser beam will take approximately 2.75 hours to complete the path.

In some embodiments, a path is chosen to avoid occluded or depleted areas of a non-linear crystal.

Figure 4:
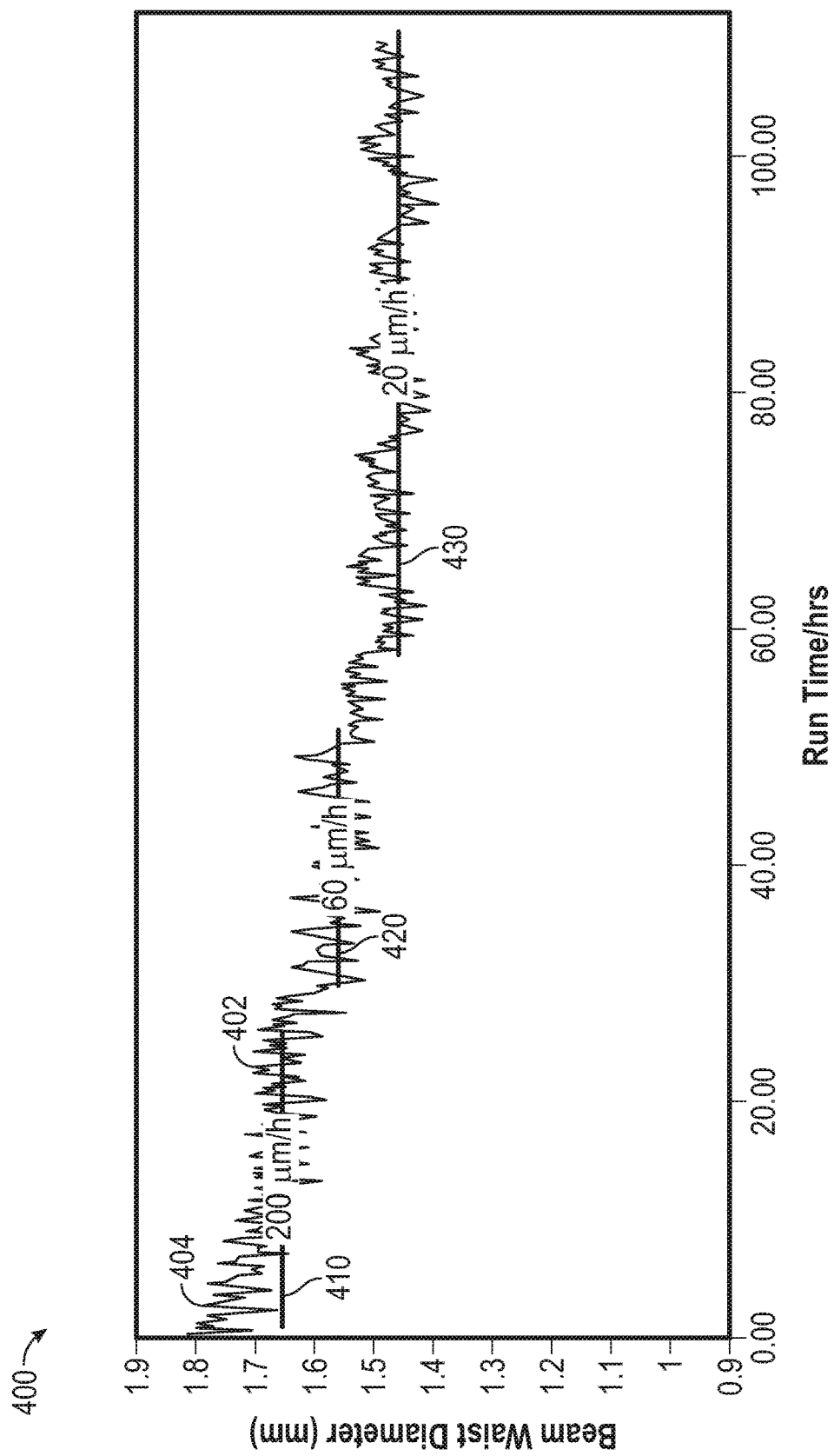
FIG. 4 is a graph of beam waist diameter versus time, in accordance with an embodiment.

FIG. 4 is a graph 400 of beam waist diameter versus time, in accordance with an embodiment. Graph 400 represents data taken from a UV beam while directing a 532 nm source beam along path 300 in FIG. 3A. The source beam had a fundamental wavelength of 532 nm and power of 15 W and was directed to a CLBO NLO crystal to produce a UV beam (SHG) of wavelength 266 nm and power of 3 W. The waist of the focused 532 nm source beam, located within the non-linear laser crystal, had an elliptical cross section of 200 µm×500 µm. The closed path length in embodiment 300 is 1000 µm and UV beam waist diameter ($2\omega_0$) was measured for a plurality of shift speeds, 200 µm/hr (identified as 410 in graph 400), 60 µm/hr (identified as 420 in graph 400), and 20 µm/hr (identified as 430 in graph 400). The cycle time for these speeds was 300 min, 1000 min, and 3000 min respectively.

As is known, the beam inside a non-linear crystal is typically a focused beam; the beam is focused to achieve the required intensity for non-linear conversion. Typically, an input beam is focused into a non-linear crystal by a lens and an output beam is collimated by another lens. In Graph 400, the beam waist diameter on the y-axis is a collimated output beam waist diameter.

Graph 400 plots the measurements of UV beam waist diameter against the run time for the plurality of shift speeds. Unexpectedly, the inventors discovered that varying shift speed affected certain beam parameters. As can be seen in Graph 400: at 200 µm/hr (identified as 410 in graph 400) the beam waist diameter is approximately 1.65 mm; at 60 µm/hr (identified as 420 in graph 400) the beam waist diameter drops to approximately 1.55 mm; and at 20 µm/hr (identified as 430 in graph 400) the beam waist diameter drops further to approximately 1.45 mm.

As disclosed herein, shifting speeds can affect beam parameters and thus a non-linear crystal's shifting speed can be utilized to control beam parameters. For example, a shifting speed can be changed to steer the beam parameter toward a target value. In some embodiments, the target value is a range and, for example, as a beam parameter degrades below a setpoint (e.g., a lower threshold of the range), the shifting speed can be decelerated to raise the beam parameter above the setpoint. Similarly, if a beam parameter is above a setpoint (e.g., an upper threshold of the range), the shifting speed can be accelerated to raise the beam parameter above the setpoint. These shifts can solely control the beam parameter or can be used in conjunction with active optics that adjust the beam parameter. As described here, shift speed can be used to stabilize the beam parameter within a feedback loop with the shifting speed as the actuating parameter to steer the actual beam parameter toward a target value.

In some embodiments, a target range is a percentage deviation from a target value. For example, a target beam waist diameter and percentage deviation might be pre-set; a measured beam waist diameter that is greater than or less than the target beam waist diameter by the percentage deviation causes an adjustment in the shift speed. A measured beam waist diameter that is within the target beam waist diameter by the percentage deviation does not cause an adjustment in shift speed. The percentage is preferably 10%, more preferably 5%, and most preferably 1%.

As can be seen in graph 400, a small initial drift (5% or less) occurs after the source beam first begins to irradiate the non-linear crystal. To accommodate this initial drift and reduce its effect on tool performance, the shifting speed can initially be relatively slow until the parameter settles to a stable level. A relatively slow speed may advantageously reduce the difference between the initial beam parameter measurement and the stable beam parameter measurement. Once the beam parameter has stabilized, a laser control unit may shift speed to achieve the desired target value. This may have the result that the shift speed starts at a first speed, the speed is increased as the beam stabilizes after an initial drift, and then the speed is changed (increased or decreased) as to steer the beam toward a target value.

Graph 400 depicts noise in the measurement of the beam waist diameter. The noise may represent the active control of the shifting speed, up and down as the servo vacillates around the target beam waist diameter.

Figure 5:
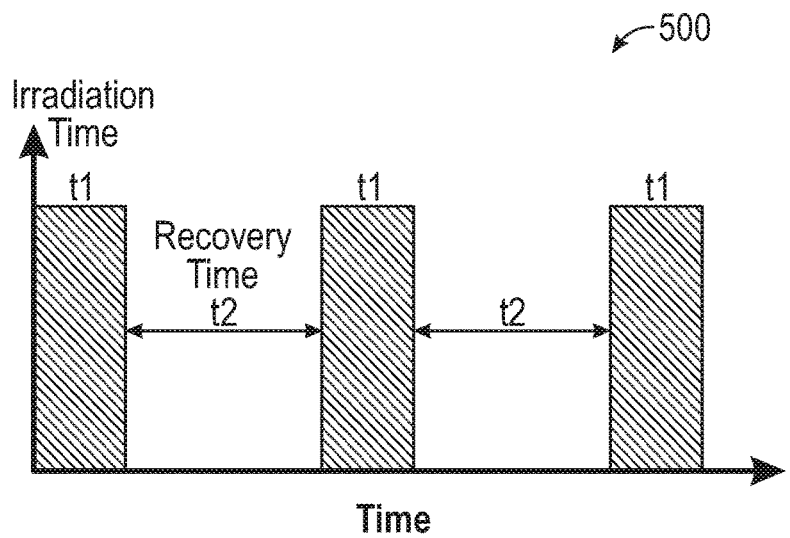
FIG. 5 is a graph of irradiation versus time, in accordance with an embodiment.
Figure 6:
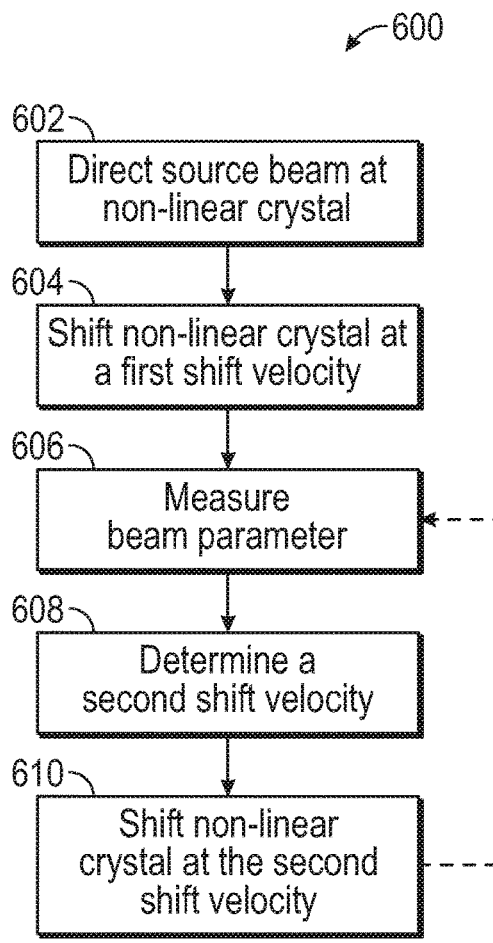
FIG. 6 is a flow chart of an embodiment of a method for controlling a UV beam.

FIG. 5 is a graph 500 of irradiation versus time, in accordance with an embodiment. Graph 500 depicts an irradiation time (t1) and a recovery time (t2) between irradiations. For example, graph 500 may depict the irradiation time and recovery time of a single spot on path 300 in FIG. 3A FIG. 6 is a flow chart of an embodiment of a method 600 for controlling a UV beam. Method 600 includes directing a source beam to a non-linear crystal to produce a UV beam 602, shifting the non-linear crystal relative to the source beam at a first shift speed 604, measuring a beam parameter of the UV beam 606, determining, based on the measured beam parameter, a second shift speed that steers the beam parameter toward a target value 608; and shifting the non-linear crystal relative to the source beam at the second shift speed 610. In some embodiments, steps 606-610 are optionally repeated (as indicated by the dashed arrow in FIG. 6).

In some embodiments, the non-linear crystal degrades during an exposure to the source beam and at least partially recovers after the exposure to the source beam. In some embodiments, shifting the non-linear crystal comprises shifting the non-linear crystal so that the source beam repeatedly traverses a path on the non-linear crystal, wherein a time between irradiations of a spot on the path is preferably at least 20 times longer than an irradiation time of the spot.

In some embodiments, the method includes determining whether the measured beam parameter is above the value and, in response to determining the measured beam parameter is above the value, determining a second shift speed faster than the first shift speed.

In some embodiments, the method includes determining whether the measured beam parameter is below the value and, in response to determining the measured beam parameter is below the value, determining a second shift speed slower than the first shift speed.

In some embodiments, the target value of the beam parameter comprises a target range of the beam parameter with an upper threshold and a lower threshold. In embodiments where the target value of the beam parameter comprises a target range, the method may further comprise determining whether the measured beam parameter is above the upper threshold, and in response to determining the measured beam parameter is above the upper threshold, determining a second shift speed faster than the first shift speed. In embodiments where the target value of the beam parameter comprises a target range, the method may further comprise determining whether the measured beam parameter is below the lower threshold, and, in response to determining the measured beam parameter is below the lower threshold, determining a second shift speed slower than the first shift speed.

In some embodiments, shifting the non-linear crystal comprises shifting the non-linear crystal so that the source beam traverses multiple serpentine paths on the non-linear crystal.

In some embodiments, shifting the non-linear crystal comprises shifting the non-linear crystal so that the source beam traverses a limited, smaller area on the crystal. In some embodiments, shifting the non-linear crystal comprises shifting multiple non-linear crystals.

In some embodiments, measuring the beam parameter comprises measuring the UV beam continuously. In some embodiments, the method further includes continuously determining, based on the continuous measurements, additional shift speeds that steer the beam parameter toward the target value, and shifting the non-linear crystal relative to the source beam at the additional shift speeds. In some embodiments, shifting the non-linear crystal comprises shifting the non-linear crystal so that the source beam repeatedly traverses a path on the non-linear crystal, and wherein the shift speed is adjusted at least once while traversing the complete path. For example, once during each completion of the path. In some embodiments, the beam parameter is measured and the speed is adjusted at a refurbishment interval.

In some embodiments, the beam parameter is one of beam quality, axial beam waist location, beam divergence, and beam waist diameter.

In some embodiments, measuring the beam parameter of the UV beam comprises measuring a process property resulting from the UV beam's interaction with a process object.

The present invention is described above with reference to preferred and other embodiments. The invention is not limited, however, to the embodiments described and depicted herein. Rather, the invention is limited only by the claims appended hereto.

What is claimed is:

1. A UV laser apparatus comprising:
   a non-linear crystal;
   a laser source configured to direct a source beam to the non-linear crystal to produce a UV beam;
   a beam-crystal displacer configured to shift the non-linear crystal relative to the source beam at a plurality of shift speeds;
   a beam parameter monitor configured to measure the UV beam and output a measurement of a size or propagation parameter of the UV beam; and
   a laser control unit configured to
      receive the measurement,
      determine, based on the measurement, an adjustment in shift speed to steer the monitored parameter toward a target value; and
      output the adjustment to the beam-crystal displacer.

2. The apparatus of claim 1, wherein the non-linear crystal degrades during an exposure to the source beam and at least partially recovers after the exposure to the source beam.

3. The apparatus of claim 1, wherein the beam-crystal displacer is configured to shift the non-linear crystal so that the source beam repeatedly traverses a path.

4. The apparatus of claim 3, wherein a time between irradiations of a spot on the path is at least 20 times longer than an irradiation time of the spot.

5. The apparatus of claim 1, wherein the beam-crystal displacer is configured to shift the non-linear crystal so that the source beam traverses a serpentine path.

6. The apparatus of claim 1, wherein the laser control unit is further configured to, upon receiving a measurement that indicates the size or propagation parameter is above the target value, output an increase in shift speed to the beam-crystal displacer and further configured to, upon receiving a measurement that indicates the size or propagation parameter is below the target value, output a decrease in shift speed to the beam-crystal displacer.

7. The apparatus of claim 1, wherein the target value of the size or propagation parameter comprises a target range of the size or propagation parameter with an upper threshold and a lower threshold.

8. The apparatus of claim 7, wherein the laser control unit is further configured to, upon receiving a measurement that indicates the size or propagation parameter is above the upper threshold, output an increase in shift speed to the beam-crystal displacer and is further configured to, upon receiving a measurement that indicates the size or propagation parameter is below the lower threshold, output a decrease in shift speed to the beam-crystal displacer.

9. The apparatus of claim 1, wherein the beam parameter monitor is configured to continuously measure the UV beam.

10. The apparatus of claim 9, wherein the laser control unit is configured to continuously output the adjustment to the beam-crystal displacer.

11. The apparatus of claim 1, wherein the beam-crystal displacer is configured to shift the non-linear crystal so that the source beam repeatedly traverses a path and wherein the shift speed is adjusted at least once while traversing the complete path.

12. The apparatus of claim 1, wherein the beam parameter monitor is configured to measure the UV beam at a refurbishment interval.

13. The apparatus of claim 1, wherein the size or propagation parameter is one of beam quality, axial beam waist location, beam divergence, and beam waist diameter.

14. The apparatus of claim 1, wherein the beam parameter monitor is configured to monitor a process property resulting from the UV beam's interaction with a process object.

15. The apparatus of claim 1, wherein the beam-crystal displacer is configured to shift the non-linear crystal relative to the source beam by one of continuous shifting, approximately continuous shifting, or step-wise shifting.

16. The apparatus of claim 15, wherein the beam-crystal displacer is configured to shift the non-linear crystal relative to the source beam by continuous shifting.

17. A method for controlling a UV beam, the method comprising:
  directing a source beam to a non-linear crystal to produce a UV beam;
  shifting the non-linear crystal relative to the source beam at a first shift speed;
  measuring a size or propagation parameter of the UV beam;
  determining, based on the measured parameter, a second shift speed that steers the parameter toward a target value of the parameter; and
  shifting the non-linear crystal relative to the source beam at the second shift speed.

18. The method of claim 17, wherein the non-linear crystal degrades during an exposure to the source beam and at least partially recovers after the exposure to the source beam.

19. The method of claim 17, wherein shifting the non-linear crystal comprises shifting the non-linear crystal so that the source beam repeatedly traverses a path on the non-linear crystal.

20. The method of claim 19, wherein a time between irradiations of a spot on the path is at least 20 times longer than an irradiation time of the spot.

21. The method of claim 17, wherein shifting the non-linear crystal comprises shifting the non-linear crystal so that the source beam traverses a serpentine path on the non-linear crystal.

22. The method of claim 17, further comprising:
  determining whether the measured parameter is above the target value; and
  in response to determining the measured parameter is above the target value, determining the second shift speed, wherein the second shift speed is faster than the first shift speed.

23. The method of claim 17, further comprising:
  determining whether the measured parameter is below the value; and
  in response to determining the measured parameter is below the value, determining the second shift speed, wherein the second shift speed is slower than the first shift speed.

24. The method of claim 17, wherein the target value of the size or propagation parameter comprises a target range of the size or propagation parameter with an upper threshold and a lower threshold.

25. The method of claim 24, further comprising:
  determining whether the measured parameter is above the upper threshold; and
  in response to determining the measured parameter is above the upper threshold, determining the second shift speed, wherein the second shift speed is faster than the first shift speed.

26. The method of claim 24, further comprising:
  determining whether the measured parameter is below the lower threshold; and
  in response to determining the measured parameter is below the lower threshold, determining the second shift speed, wherein the second shift speed is slower than the first shift speed.

27. The method of claim 17, wherein measuring the size or propagation parameter comprises continuously measuring the UV beam.

28. The method of claim 27, further comprising
  continuously determining, based on the continuous measurements, additional shift speeds that steer the size or propagation parameter toward the target value; and
  shifting the non-linear crystal relative to the source beam at the additional shift speeds.

29. The method of claim 17, wherein shifting the non-linear crystal comprises shifting the non-linear crystal so that the source beam repeatedly traverses a path on the non-linear crystal, and wherein shifting at the second shift speed comprises shifting at the second shift speed at least once while traversing the complete path.

30. The method of claim 17, wherein measuring the size or propagation parameter comprises measuring the UV beam at a refurbishment interval.

31. The method of claim 17, wherein the size or propagation parameter is one of beam quality, axial beam waist position, beam divergence, and beam waist diameter.

32. The method of claim 17, wherein measuring the size or propagation parameter of the UV beam comprises measuring a process property resulting from the UV beam's interaction with a process object.

33. The method of claim 17, wherein shifting the non-linear crystal relative to the source beam at a first shift speed comprises shifting the non-linear crystal relative to the source beam by one of continuous shifting, approximately continuous shifting, or step-wise shifting.

34. The method of claim 33, wherein shifting the non-linear crystal relative to the source beam at a first shift speed comprises continuous shifting of the non-linear crystal relative to the source beam.

* * * * *